(12) United States Patent
Konings et al.

(10) Patent No.: US 6,530,889 B1
(45) Date of Patent: Mar. 11, 2003

(54) CATHETER SYSTEM AND CATHETER TO BE USED THEREIN

(75) Inventors: Maurits Karel Konings; Lambertus Wilhelmus Bartels, both of Utrecht (NL)

(73) Assignee: Centrum RRN Academisch Ziekenhuis Utrecht, Utrecht (NL)

( * ) Notice: Subject to any disclaimer, the term of this patent is extended or adjusted under 35 U.S.C. 154(b) by 0 days.

(21) Appl. No.: 09/348,250

(22) Filed: Jul. 6, 1999

(30) Foreign Application Priority Data

Jul. 6, 1998 (NL) .............................................. 1009565

(51) Int. Cl.⁷ .................................................. A61B 5/02
(52) U.S. Cl. ......................... 600/486; 600/561; 606/15
(58) Field of Search .................................. 600/300, 310, 600/374, 485–486, 561; 606/26–28, 13–18, 33–50, 149; 73/720, 800

(56) References Cited

U.S. PATENT DOCUMENTS

| | | | |
|---|---|---|---|
| 4,659,923 A | 4/1987 | Hicks, Jr. ................... 250/227 |
| 4,691,709 A | 9/1987 | Cohen .......................... 128/667 |
| 4,730,622 A | * 3/1988 | Cohen .......................... 600/488 |
| 5,059,396 A | 10/1991 | Opitz et al. ............... 422/82.11 |
| 5,178,153 A | 1/1993 | Einzig .......................... 128/692 |
| 5,280,786 A | * 1/1994 | Wlodarczyk et al. ........ 600/327 |
| 5,419,312 A | * 5/1995 | Arenberg et al. ............ 600/549 |
| 5,425,273 A | * 6/1995 | Chevalier ..................... 600/488 |
| 5,475,489 A | 12/1995 | Göttsche ...................... 356/364 |
| 5,495,850 A | 3/1996 | Zuckerman .................. 128/634 |
| 5,533,515 A | 7/1996 | Coller et al. ................. 128/748 |

OTHER PUBLICATIONS

Dutch Search Report No. 1009565 dated Jan. 28, 1999.

* cited by examiner

*Primary Examiner*—Cary O'Connor
*Assistant Examiner*—Ryan Carter
(74) *Attorney, Agent, or Firm*—Darby & Darby

(57) ABSTRACT

The invention relates to a catheter system adapted for pressure sensing. It comprises a transmitter/receiver for polarized light and an optical fiber to be connected to said transmitter/receiver, said fiber at its distal end being provided with a cylindrical body of transparent plastic material, and said body having a hollow central inner lumen provided around its longitudinal axis, and said cylindrical body is provided with a mirror at its side facing away from said fiber.

13 Claims, 2 Drawing Sheets

CATHETER SYSTEM AND CATHETER TO BE USED THEREIN

BACKGROUND OF THE INVENTION

The invention relates to a catheter system adapted for pressure sensing.

DESCRIPTION OF THE RELATED ART

Such a catheter system is used for percutane transluminal angioplastic. During the treatment of stenosis of blood vessels is it important to be able to measure the blood pressure instantaneously. By measuring the amount of blood flow concurrently with measuring the pressure, one obtains information regarding the degree of obstruction, provided that pressure sensing is accurate. Prior art pressure sensing systems usually are not. Known is for instance a system for measuring pressure at an opening at the end of a catheter, or a measuring system in which the pressure is measured unilaterally through a small hole in the side of the catheter. The fact that the pressure measurement at an opening at the end of the catheter, the normal of the opening being substantially parallel to the direction of the blood flow, is inaccurate follows from the law of Bernouilli. Unilateral pressure measurement through a small hole in the side of the catheter is problematic because the pressure measurement in that case is dependent on the accidental rotational position of the catheter about its longitudinal axis. The pressure distribution around the catheter is hardly ever homogeneous, since the catheter merely always lies against the wall of the blood vessel in which it is present.

SUMMARY OF THE INVENTION

It is a first goal of the invention to provide a catheter system for being able to perform an accurate pressure measurement.

It is a second goal of the invention to provide a catheter system that may be used in so-called interventional MRI. Interventional MRI is a treatment technique in which the patient undergoes treatment when being in a magnet scanner (MRI). By providing a catheter system that may be used during this treatment, important advantages for treatment can be reached since the surgeon may obtain current information.

It is a third goal of the invention to provide a catheter system with which also rapid pressure changes can be recorded well in time, without pressure pulses, such as those originating from the heart beat, being smoothed.

These goals are achieved by the catheter system according to the invention being characterized in that it comprises a transmitter/receiver for polarized light and an optical fiber to be connected to said transmitter/receiver, said fiber at its distal end being provided with a cylindrical body of transparent plastic material, and said body having a hollow central inner lumen provided around its longitudinal axis, and in that said cylindrical body is provided with a mirror at its side facing away from said fiber. The invention is also embodied in a separate catheter which may or may not be used as a guiding thread in said catheter system, and which according to the invention at its distal end is provided with a cylindrical body of transparent plastic material, said body having a hollow central inner lumen provided around its longitudinal axis, and said cylindrical body being provided with a mirror at the side facing away from said fiber. Such a catheter lacks ferromagnetic materials and long electrical conductors which would prevent use of the catheter in interventional MRI. Preferably A-PET is being used as the plastic material.

The invention is based on the understanding that the cylindrical body of transparent plastic material which is provided at the distal end of the optical fiber has birefringent characteristics which are dependent on the pressure present on the outside of the body, i.e. the propagation speed of the laser light travelling through the plastic body is dependent on the direction of polarization of said light. When a pressure is present on the outside of the cylindrical body, part of the light of a first polarization state converts to a second polarization state, said second state being perpendicular to the original polarization state. The degree of the conversion is dependent on the pressure exerted on the cylindrical body. Measuring the amount of light converted in polarization direction yields an indirect measure of the pressure. By constructing the plastic body cylindrical one obtains in addition a symmetrical pressure sensor which is sensitive on all sides, the rotational position of the catheter not being important.

It is desirable that a lens is provided in between said distal end of said fiber and said cylindrical body. The lens is being employed to transform the divergent light leaving the fiber into a collimated beam of polarized laser light.

Furthermore, it is desirable that the inner lumen at its side facing away from said fiber is provided with a black body. This has the effect that the light propagating through the inner lumen is extinguished, and guarantees that the light reflected by the mirror passes the plastic body twice.

For a good operation of the catheter system according to the invention, it is desirable that said transmitter/receiver comprises a laser source and a first polarization filter arranged in between said laser source and a beam splitter having a fixed polarization. The first polarization filter is being employed to condition the light originating from the laser source for the pressure measurement.

It is furthermore desirable that a second polarization filter and a detector positioned behind said second polarization filter are connected to said beam splitter.

Measuring the pressure with the catheter system according to the invention is easily realized when said first and second polarization filters polarize the laser light mutually orthogonal.

BRIEF DESCRIPTION OF THE DRAWINGS

The invention is further embodied in the separate catheter adapted for employment in the catheter system mentioned above.

The invention will be further elucidated with the aid of the drawing, in which.

In the figures identical reference numerals refer to identical parts.

DETAILED DESCRIPTION OF THE PREFERRED EMBODIMENT

Figure 1:
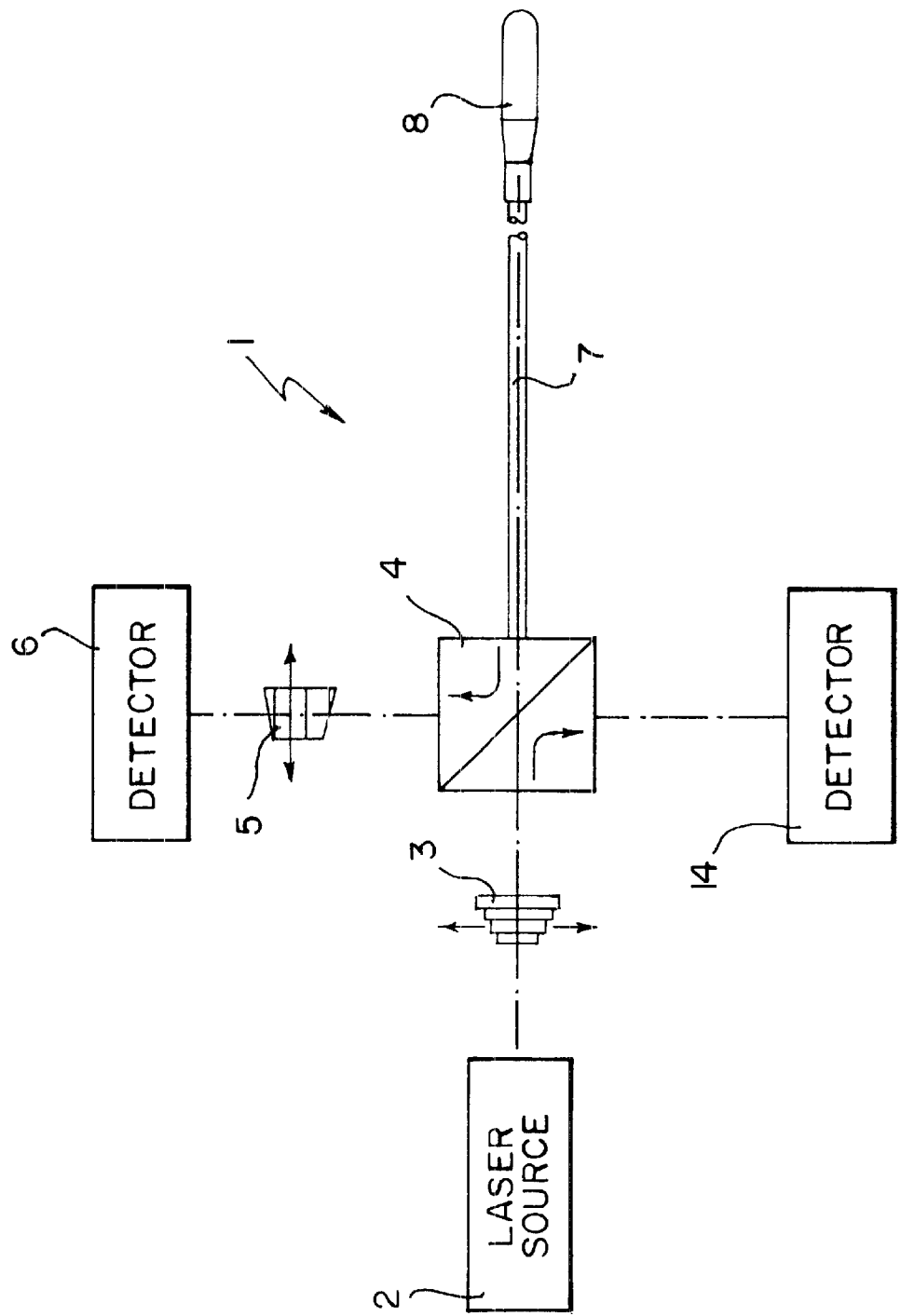
FIG. 1 shows the catheter system according to the invention.

Referring first to FIG. 1, a catheter system 1 is shown, which according to the invention comprises a transmitter/ receiver 2, 3, 4, 5, 6 for polarized light, and an optical fiber 7 to be connected to said transmitter/receiver 2, 3, 4, 5, 6, said optical fiber being provided at its distal end 8 with a cylindrical body 9 of transparent plastic material. The transparent plastic material is preferably A-PET.

Figure 2:
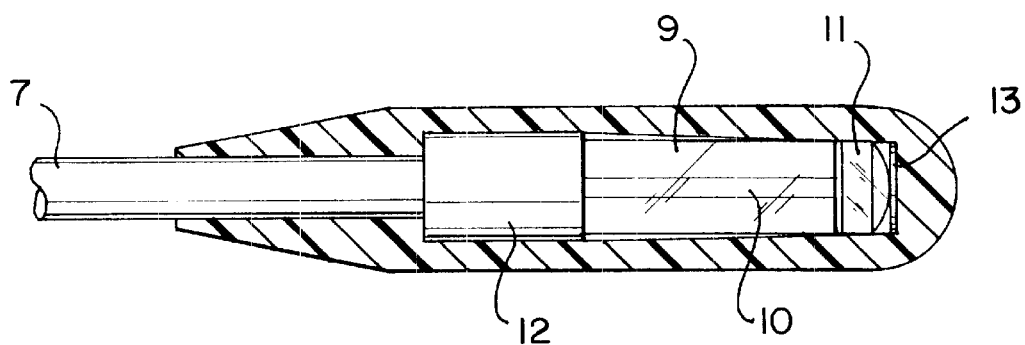
FIG. 2 shows in detail the distal end of the catheter according to the invention.
Figure 3:
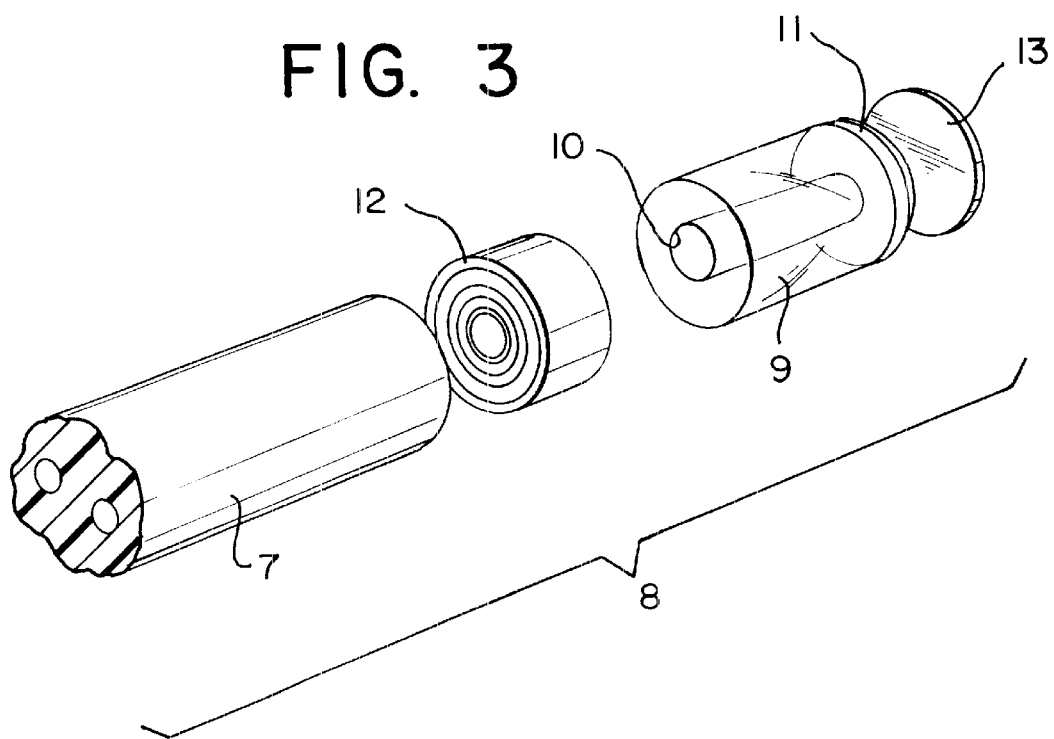
FIG. 3 shows in diagrammatic exploded view the distal end of the catheter according to the invention.

FIG. 3 shows clearly that the cylindrical body 9 has a hollow central inner lumen 10 provided along its longitudinal axis. The cylindrical body 9 further has a mirror 11 at the side facing away from the fiber 7. A lens 12 is in addition provided in between the distal end of the fiber 7 and the cylindrical body 9. This is clearly shown in FIGS. 1, 2 and 3. The inner lumen 10 further has a black body 13 at the side facing away from the fiber 7.

Referring again to FIG. 1, it is shown that the transmitter/receiver 2, 3, 4, 5, 6 comprises a laser source 2, and a first polarization filter 3 arranged in between the laser source 2 and a beam splitter 4 having a fixed polarization. The transmitter/receiver further comprises a second polarization filter 5 connected to the beam splitter 4, and a detector 6 provided behind the second polarization filter 5. The first polarization filter 3 and the second polarization filter 5 polarize the light originating from the laser source 2 mutually orthogonal.

The operation of the catheter system 1 according to the invention is as follows. The laser light leaves the laser 2 and is splitted in two parts in the beam splitter 4 after being polarized by the first polarization filter 3. Half of the polarized light proceeds through the fiber 7. The other half may be used in a further detector 14 for monitoring the laser intensity. The fiber 7 is adapted for guiding the light in at least two orthogonal polarization states. The light polarized in a first state by the first polarization filter 3 is transformed into a collimated beam at its distal end with a lens 12, said beam propagating through the plastic material of the cylindrical body 9. The light travelling through the central inner lumen 10 of the cylindrical body 9 is absorbed by a black body 13 positioned at the end of the inner lumen 10. The cylindrical body 9 shows at its inside an inner pressure given by the pressure in the inner lumen 10. The outside pressure on the cylindrical body 9 is given by the blood pressure. The inner pressure and the outer pressure determine the degree in which the light propagating through the cylindrical body 9 is modified in polarization direction. After the light has been reflected by the mirror 11 it proceeds back through the fiber 7, is received in the beam splitter 4 where it is splitted, and half of the reflected light arrives at the second polarization filter 5 of which the polarization direction is oriented perpendicular with respect to the first polarization filter 3. A detector 6 is connected to the second polarization filter 5 for measuring the light intensity of the light having passed the second polarization filter 5. Said light intensity measured by detector 6 is an indirect measure for the pressure present around the cylindrical body 9.

What is claimed is:

1. Catheter system adapted for pressure sensing, comprising: a transmitter/receiver for polarized light and an optical fiber connectable to said transmitter/receiver, said fiber at its distal end being provided with a cylindrical body of transparent plastic material, and said body having a hollow central inner lumen provided around its longitudinal axis and a mirror disposed at a side of the cylindrical body facing away from said fiber.

2. Catheter system according to claim 1, wherein said plastic material is polyethylene terephthalate.

3. The catheter according to claim 2, wherein said plastic material comprises A-PET.

4. Catheter system according to claim 1, further comprising a lens disposed between said distal end of said fiber and said cylindrical body.

5. Catheter system according to claim 1, wherein said inner lumen at its side facing away from said fiber is provided with a black body.

6. Catheter system according to claim 1, wherein said transmitter/receiver comprises a laser source and a first polarization filter arranged in between said laser source and a beam splitter having a fixed polarization.

7. Catheter system according to claim 6, further comprising a second polarization filter and a detector positioned behind said second polarization filter, said detector and said second polarization filter are connected to said beam splitter.

8. Catheter system according to claim 7, wherein said first and second polarization filters polarize the laser light in mutually orthogonal directions.

9. Catheter, comprising: an optical fiber which at its distal end is provided with a cylindrical body of transparent plastic material, and said body having a hollow central inner lumen provided around its longitudinal axis, and in that said cylindrical body is provided with a mirror at its side facing away from said fiber.

10. Catheter according to claim 9, wherein said plastic material is polyethylene terephthalate.

11. The catheter according to claim 10, wherein said plastic material comprises A-PET.

12. Catheter according to claim 9, further comprising a lens disposed between said distal end of said fiber and said cylindrical body.

13. Catheter according to claim 9, wherein said inner lumen at its side facing away from said fiber is provided with a black body.

* * * * *